US011077124B2

(12) United States Patent
Malhotra et al.

(10) Patent No.: US 11,077,124 B2
(45) Date of Patent: Aug. 3, 2021

(54) PHARMACEUTICAL COMPOSITIONS

(71) Applicant: CIPLA Limited, Mumbai (IN)

(72) Inventors: Geena Malhotra, Maharashtra (IN); Shrinivas Madhukar Purandare, Maharashtra (IN); Amar Lulla, Maharashtra (IN)

(73) Assignee: CIPLA Limited, Mumbai (IN)

( * ) Notice: Subject to any disclaimer, the term of this patent is extended or adjusted under 35 U.S.C. 154(b) by 0 days.

(21) Appl. No.: 15/645,513

(22) Filed: Jul. 10, 2017

(65) Prior Publication Data

US 2017/0333452 A1 Nov. 23, 2017

Related U.S. Application Data

(60) Division of application No. 13/962,094, filed on Aug. 8, 2013, now abandoned, which is a continuation of application No. 13/810,656, filed as application No. PCT/GB2011/001077 on Jul. 18, 2011, now abandoned.

(30) Foreign Application Priority Data

| Jul. 16, 2010 | (IN) | 2051/MUM/2010 |
| Nov. 18, 2010 | (IN) | 3156/MUM/2010 |
| Nov. 18, 2010 | (IN) | 3157/MUM/2010 |

(51) Int. Cl.

| A61K 31/46 | (2006.01) |
| A61K 31/58 | (2006.01) |
| A61K 31/137 | (2006.01) |
| A61K 31/138 | (2006.01) |
| A61K 31/167 | (2006.01) |
| A61K 31/4704 | (2006.01) |
| A61K 31/4709 | (2006.01) |
| A61K 9/00 | (2006.01) |
| A61K 45/06 | (2006.01) |

(52) U.S. Cl.
CPC .............. *A61K 31/58* (2013.01); *A61K 9/008* (2013.01); *A61K 9/0075* (2013.01); *A61K 31/137* (2013.01); *A61K 31/138* (2013.01); *A61K 31/167* (2013.01); *A61K 31/46* (2013.01); *A61K 31/4704* (2013.01); *A61K 31/4709* (2013.01); *A61K 45/06* (2013.01)

(58) Field of Classification Search
CPC ...... A61K 31/46; A61K 31/58; A61K 31/137; A61K 31/138; A61K 31/4709; A61K 31/4704
See application file for complete search history.

(56) References Cited

U.S. PATENT DOCUMENTS

| 7,348,362 B2 * | 3/2008 | Banerjee .............. A61K 9/0078 |
| | | 514/651 |
| 8,313,732 B2 | 11/2012 | Davies et al. |
| 9,295,644 B2 | 3/2016 | Ekstrom |
| 9,446,054 B2 | 9/2016 | Lulla et al. |
| 2003/0190289 A1 | 10/2003 | Lewis et al. |
| 2007/0020190 A1 | 1/2007 | Razzetti et al. |
| 2008/0004247 A1 | 1/2008 | Lindmark et al. |
| 2009/0088408 A1 | 4/2009 | Meade et al. |
| 2009/0298802 A1 | 12/2009 | Sequeira et al. |
| 2013/0074834 A1 | 3/2013 | Lulla et al. |

FOREIGN PATENT DOCUMENTS

| CN | 1753678 A | 3/2006 |
| CN | 1984653 A | 6/2007 |
| CN | 101249093 A | 8/2008 |
| JP | 2002517450 A | 6/2002 |
| JP | 2004515454 A | 5/2004 |
| JP | 2005502608 A | 1/2005 |
| JP | 2005524664 A | 8/2005 |
| JP | 2005539046 A | 12/2005 |
| JP | 2008534611 A | 8/2008 |
| JP | 2010519195 A | 6/2010 |
| WO | 9964014 | 12/1999 |
| WO | 03074025 A2 | 9/2003 |
| WO | 2008102128 A2 | 8/2008 |

OTHER PUBLICATIONS

King (Int j Chron Obstruct pulmon Dis, Sep. 2008; 3(30):385-392).*
Brovana, Rxlist.*
EP Communication pursuant to Article 94(3) EPC, Application No. 11738260.6, dated Jun. 20, 2017.
Korean Office Action, Application No. 1020137003819, dated Apr. 11, 2017.
Japanese Final Office Action, Application No. JP 2016-185143, dated Apr. 3, 2018.
Brovana, RxList, Drug Description, https://www.rxlist.com/brovana-drug.htm., dated Oct. 15, 2017, pp. 1-41.
Chinese Office Action, Application No. 201510665216.4, dated Aug. 1, 2017.

(Continued)

*Primary Examiner* — Zohreh A Fay
(74) *Attorney, Agent, or Firm* — MacMillan, Sobanski & Todd, LLC

(57) ABSTRACT

A pharmaceutical composition for inhalation comprising R (+) budesonide and one or more bronchodilators, and, optionally, one or more pharmaceutically acceptable excipients is described.

22 Claims, No Drawings

(56) References Cited

OTHER PUBLICATIONS

King, "Role of arformoterol in the management of COPD", International Journal of Chronic Obstructive Pulmonary Disease, Sep. 2008, 3(3), pp. 385-392.
Korean Decision of Rejection, Application No. KR 10-2013-7003819, dated Mar. 29, 2018.
Korean Re-Examination Decision of Rejection, Application No. KR 10-2013-7003819, dated Jul. 9, 2018.
Korean Official Action, Application No. KR 10-2018-7022543 dated Jan. 2, 2019.

\* cited by examiner

PHARMACEUTICAL COMPOSITIONS

CROSS-REFERENCE TO RELATED CASES

This application is filed under 35 U.S.C. § 111(a) as a divisional application which claims priority under 35 U.S.C. § 119, 35 U.S.C. § 120, and the Patent Cooperation Treaty to: parent application U.S. application Ser. No. 13/962,094, filed under 35 U.S.C. § 111(a) on Aug. 8, 2013, published; which claims priority to U.S. application Ser. No. 13/810, 656, filed under 35 U.S.C. § 371 on Jan. 16, 2013, published; which claims priority to international application PCT/GB2011/001077, filed under the authority of the Patent Cooperation Treaty on Jul. 18, 2011, published; which claims priority to Indian Application Ser. No. 2051/MUM/2010, filed Jul. 16, 2010, Ser. No. 3157/MUM/2010, filed Nov. 18, 2010, and Ser. No. 3156/MUM/2010, filed Nov. 18, 2010. All of the aforementioned applications are expressly incorporated herein by reference for all purposes.

FIELD OF INVENTION

The present invention relates to pharmaceutical products and formulations comprising R (+) budesonide. More particularly the present invention relates to pharmaceutical products and formulations comprising R (+) budesonide, which products and formulations are useful for the treatment and/or prevention of respiratory, inflammatory or obstructive airway disease. The present invention also relates to a process for preparing the formulation according to the present invention, therapeutic uses thereof and methods of treatment employing the same.

BACKGROUND AND PRIOR ART

Asthma and chronic obstructive pulmonary disease (COPD) are the most prevailing conditions which affect most people. Airflow obstruction is the main characteristic feature in each of these airway diseases and the medications utilized in the treatment are also often similar. The pathophysiology of asthma and related disorders involves various symptoms, including bronchoconstriction, inflammation of the airways, and increased mucous secretion, which results in wheezing, coughing and shortness of breath. A persistent or recurrent cough may exacerbate the problem by causing further irritation and inflammation of the airways. Bronchoconstriction occurs due to bronchial smooth muscle spasm and airway inflammation with mucosal edema. COPD is a severe respiratory condition that is increasing its prevalence worldwide. In India, the estimated prevalence is about 12.36 million. It is currently the fourth leading cause of death in the UK & US, and predicted to rank third in the global impact of disease by the year 2020. COPD is a preventable and treatable disease state characterized by air flow limitation that is not fully reversible. The airflow obstruction is usually progressive and associated with an abnormal inflammatory response of the lungs to noxious particles or gases, primarily caused by cigarette smoking. Although COPD affects the lungs it also produces significant systemic consequences. COPD is associated with mucus hyper secretion, emphysema and bronchiolitis.

Therapy for the treatment or prevention of COPD and asthma currently includes the use of bronchodilators such as beta$_2$-agonists, anticholinergics and steroids.

Inhaled bronchodilators are the foundation of pharmacotherapy for COPD because of their capacity to alleviate symptoms, decrease exacerbations of disease and improve quality of life. These drugs also improve airflow limitation and hyperinflation, thereby improving exercise tolerance. In addition bronchodilators may reduce respiratory muscle fatigue (controversial) and improve mucociliary clearance.

Long acting beta$_2$-agonists improve lung function, reduce symptoms and protect against exercise-induced dyspnea in patients with asthma and COPD. Long acting beta$_2$-agonists induce bronchodilation by causing prolonged relaxation of airway smooth muscle. In addition to prolonged bronchodilation, long acting beta$_2$-agonists (LABAs) exert other effects such as inhibition of airway smooth-muscle cell proliferation and inflammatory mediator release, as well as non smooth-muscle effects, such as stimulation of mucociliary transport, cytoprotection of the respiratory mucosa and attenuation of neutrophil recruitment and activation.

Long acting beta$_2$-agonists reduce the symptoms that occur in the night or the early morning which normally affect sleep patterns and reduce a patient's overall quality of life.

Further, use of a long acting beta$_2$-agonist reduces the frequency of drug administration.

Anticholinergic agents are also a first choice for the symptomatic treatment of patients with COPD.

Anticholinergic agents inhibit the muscarinic action of acetylcholine on structure innervated by postganglionic cholinergic nerves. These agents typically inhibit bronchoconstriction by relaxing the smooth muscles and causing considerable bronchodilation.

Even though it is also known that beta$_2$-agonists and anticholinergics provide a symptomatic relief in bronchoconstriction, another component of asthma, which is inflammation, requires separate treatment such as with a steroid. Most of these inhaled corticosteroids need to be administered in multiple dosage regimens.

Treatment with a corticosteroid/glucocorticoid is considered to be one of the most potent and effective therapies currently available for persistent asthma. Corticosteroids exhibit inhibitory effects on inflammatory cells and inflammatory mediators involved in the pathogenesis of respiratory disorders.

Corticosteroids are used in several forms, to treat many different conditions. Because they reduce itching, swelling, redness, and allergic reactions, they are often used in treating skin problems, severe allergies, asthma, and arthritis.

Currently available corticosteroids include beclomethasone, budesonide, fluticasone, mometasone and triamcinolone.

Combination therapy of a long-acting beta$_2$-agonist, an anticholinergic and an inhaled corticosteroid improves pulmonary efficiency, reduces inflammatory response and provides symptomatic relief as compared to higher doses of inhaled corticosteroid alone in patients affected by respiratory disorders such as asthma and COPD. However, the selection of a specific long-acting beta$_2$-agonist, a specific anticholinergic and a specific inhaled corticosteroid plays a very important role in formulation of a fixed dose combination.

Combination therapy also simplifies treatment of respiratory disorders, reduces the cost of treatment and provides control of the respiratory disorders. Reducing the dose frequency to the minimum is a main step in simplifying COPD and asthma management for improving patient adherence to the therapy.

US2009088408 discloses pharmaceutical compositions of anticholinergics, corticosteroids and betamimetics and their use in the treatment of respiratory diseases.

US20050042174 discloses combined doses of asthma medicaments such as a combination of doses of a beta$_2$-agonist, an anticholinergic agent and an anti-inflammatory steroid.

WO2006105401 discloses combination of an anticholinergic, a corticosteroid and a long acting beta$_2$-agonist for simultaneous and sequential administration in the prevention or treatment of a respiratory, inflammatory or obstructive airway disease.

WO2004028545 discloses a combination of a long-acting beta$_2$-agonist and a glucocorticosteroid in the treatment of fibrotic diseases.

However, uses of corticosteroids, especially in children, have been limited due to potential side effects. In children and teenagers, these medicines can stop or slow growth and affect the function of the adrenal glands (small glands located above each kidney, which secrete natural corticosteroids). Another possible problem for children is that corticosteroids may make infections such as chickenpox and measles more serious.

The other side effects that are feared with corticosteroids include suppression of the Hypothalamic-Pituitary-Adrenal (HPA) axis, effects on bone growth in children and on bone density in the elderly, ocular complications (cataract formation and glaucoma) and skin atrophy. In older people, corticosteroids may increase the risk of high blood pressure and bone disease. Bone problems from corticosteroids are especially likely in older women.

The benefits and risks of giving corticosteroids to children and teenagers should be thoroughly discussed with a physician. By adjusting the doses and forms in which corticosteroids are given, a physician may be able to lower the chance of unwanted side effects.

Some corticosteroids exist as enantiomers and exhibit chirality. Enantiomers are structurally identical compounds which differ only in that, one isomer is a mirror image of the other and the mirror images cannot be superimposed. This phenomenon is known as chirality. Although structurally identical, enantiomers can have profoundly different effects in biological systems; one enantiomer may have a specific biological activity while the other enantiomer may have no biological activity at all, or may have an entirely different form of biological activity. Budesonide, a corticosteroid, has been widely used in the treatment of chronic and asthmatic bronchitis due to its strong anti-inflammatory action, high selectivity and fewer side effects. The form in which budesonide is presently used is a racemic mixture. That is, it is a mixture of optical isomers, called enantiomers R (+) and S (−), which are characterized by different strength and pharmacokinetic properties.

Budesonide, is chemically a mixture of two epimers 22R (+) and 22S (−) having a different configuration at the acetal 22-carbon atom. R (+) budesonide, which consists mainly of epimer 22R, is found to be clinically superior over the preparations consisting of a 1:1 mixture of the epimers.

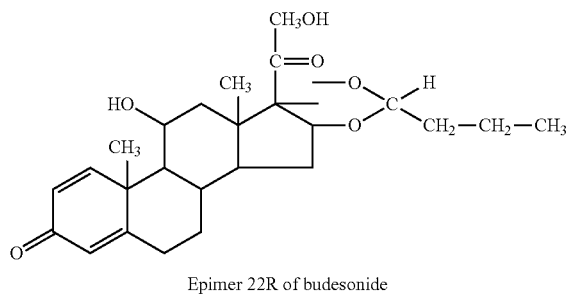

Epimer 22R of budesonide

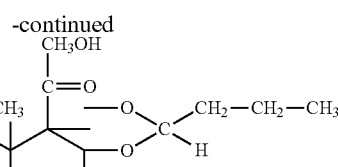

Epimer 22S of budesonide

The anti-inflammatory properties of R (+) isomer are nearly three times as strong as compared to that of S (−) isomer. R (+) budesonide also shows greater volume of distribution and plasma clearance. R (+) budesonide is very well tolerated and does not cause any serious adverse effects. However as R (+) budesonide undergoes biotransformation more quickly than S (−) isomer, the systemic action of R (+) budesonide is weaker as compared to that of S (−) budesonide. Budesonide is the mainstay in the treatment of respiratory and inflammatory or obstructive airway diseases. However most of the formulations containing budesonide available in the prior art contain the racemic mixture of budesonide.

Hence, there still remains a need to formulate pharmaceutical compositions comprising R (+) budesonide for inhalation having reduced side effects, and to formulate pharmaceutical compositions comprising R (+) budesonide in combination with one or more bronchodilators for inhalation having reduced side effects.

OBJECT OF THE INVENTION

The object of the present invention is to provide novel pharmaceutical compositions for inhalation comprising R (+) budesonide and one or more bronchodilators for administration in the prevention or treatment of respiratory, inflammatory or obstructive airway disease.

Another object of the present invention is to provide novel pharmaceutical compositions for inhalation comprising R (+) budesonide and one or more bronchodilators for inhalation having reduced side effects in the prevention or treatment of respiratory, inflammatory or obstructive airway disease.

The compositions according to the invention may, of course, include one or more pharmaceutically acceptable excipients.

Yet another object of the present invention is to provide a process for preparing novel pharmaceutical compositions comprising R (+) budesonide and one or more bronchodilators for administration in the prevention or treatment of respiratory, inflammatory or obstructive airway disease.

A further object of the present invention is to provide pharmaceutical compositions comprising R (+) budesonide and one or more bronchodilator for use in the prophylaxis or treatment of respiratory, inflammatory or obstructive airway disease.

SUMMARY OF THE INVENTION

According to a first aspect of the present invention, there is provided a pharmaceutical composition comprising R (+) budesonide and one or more bronchodilators.

According to a second aspect of the present invention, there is provided a process for preparing a pharmaceutical composition comprising R (+) budesonide and one or more bronchodilators.

According to a third aspect of the present invention there is provided a pharmaceutical composition comprising R (+) budesonide and one or more bronchodilators for use in treating disorders or conditions that respond to, or are prevented, ameliorated or eliminated by, the administration of R (+) budesonide, and one or more bronchodilators.

DETAILED DESCRIPTION OF THE INVENTION

It has been found that the R (+) enantiomer of budesonide provides relief from bronchial disorders, while simultaneously reducing undesirable side effects commonly experienced by corticosteroid users. Further since the active enantiomer is used, the dose required is also reduced as compared to that of racemic budesonide, which reduced dose also contributes to the reduction in undesirable side effects.

The present invention thus provides novel pharmaceutical compositions for inhalation comprising R (+) budesonide and one or more bronchodilators for administration in the prevention or treatment of respiratory, inflammatory or obstructive airway disease while simultaneously reducing undesirable side effects commonly experienced by corticosteroid users.

According to the present invention, the optically pure R (+) isomer of budesonide may be administered alone, or in combination with one or more bronchodilators or other drug(s) for the treatment and/or prevention of respiratory, inflammatory or obstructive airway disease.

The other drugs may be selected from various classes of drugs commonly used for respiratory diseases for example bronchodilators.

The present invention provides a pharmaceutical composition comprising R (+) budesonide and one or more bronchodilators.

Bronchodilators used according to the present invention may be beta$_2$-agonists and/or anticholinergics. As discussed, the selection of a specific long-acting beta$_2$-agonist, an anticholinergic and inhaled corticosteroid plays a very important role in formulation of fixed dose combination.

The terms "beta$_2$-agonist agent" or "beta$_2$-agonist" or "anticholinergic agent" or "corticosteroids" are used in broad sense to include not only the beta$_2$-agonist or anticholinergic agent per se but also their pharmaceutically acceptable salts, pharmaceutically acceptable solvates, pharmaceutically acceptable hydrates, pharmaceutically acceptable enantiomers, pharmaceutically acceptable derivatives, pharmaceutically acceptable enantiomers, pharmaceutically acceptable polymorphs, pharmaceutically acceptable prodrugs, etc.

The present invention also provides a pharmaceutical composition comprising R (+) budesonide and one or more beta$_2$-agonists.

According to the present invention, beta$_2$-agonists may comprise, one or more, short acting beta$_2$-agonists, long acting beta$_2$-agonists or ultra long acting beta$_2$-agonists.

The beta$_2$-agonists that can be used, according to the present invention, include albuterol, levoalbuterol, terbutaline, pirbuterol, procaterol, metaproterenol, fenoterol, bitolterol mesylate, ritodrine, salmeterol, formoterol, arformoterol, carmoterol, bambuterol, clenbuterol, indacaterol, milveterol, vilanterol, olodaterol.

According to one embodiment of the present invention the pharmaceutical composition may comprise R (+) budesonide and formoterol with one or more pharmaceutically acceptable excipients, R (+) budesonide and arformoterol with one or more pharmaceutically acceptable excipients, R (+) budesonide and salmeterol with one or more pharmaceutically acceptable excipients.

According to another embodiment of the present invention the pharmaceutical composition may comprise R (+) budesonide, and carmoterol with one or more pharmaceutically acceptable excipients.

According to yet another embodiment of the present invention the pharmaceutical composition may comprise R (+) budesonide, and indacaterol with one or more pharmaceutically acceptable excipients.

The present invention also provides a pharmaceutical composition comprising R (+) budesonide and one or more anticholinergic agent.

Suitable anticholinergic agents include tiotropium, ipratropium and oxitropium.

According to one embodiment of the present invention the pharmaceutical composition may comprise R (+) budesonide and tiotropium with one or more pharmaceutically acceptable excipients, or R (+) budesonide and ipratropium with one or more pharmaceutically acceptable excipients, or R (+) budesonide and oxitropium with one or more pharmaceutically acceptable excipients.

The present invention also provides a pharmaceutical composition comprising R (+) budesonide and one or more beta-agonist and one or more anticholinergic agents.

According to an embodiment of the present invention the pharmaceutical composition may comprise R (+) budesonide, arformoterol and tiotropium with one or more pharmaceutically acceptable excipients, or R (+) budesonide, arformoterol and tiotropium with one or more pharmaceutically acceptable excipients or R (+) budesonide, tiotropium and carmoterol with one or more pharmaceutically acceptable excipients, or R (+) budesonide, tiotropium and indacaterol with one or more pharmaceutically acceptable excipients.

A preferred beta$_2$-agonist for use in the present invention is carmoterol.

Carmoterol, chemically known as 8-hydroxy-5-(1-hydroxy-2-(N-(2-(4-methoxy phenyl)-1-methyl ethyl) amino) ethyl)-2(1H)-quinolinone hydrochloride salt is a long acting beta$_2$-agonist characterized by having a rapid onset of action s, prolonged duration of action and also having a high selectivity towards the beta$_2$ adrenoreceptor. Furthermore carmoterol is more potent than other long acting beta$_2$-agonists.

Another preferred beta$_2$-agonist for use in the present invention is indacaterol.

Indacaterol is chemically known as (R)-5-[2-[(5,6-diethyl-2,3-dihydro-1H-inden-2-yl)amino]-1-hydroxy ethyl]-8-hydroxy quinolin-2(1H)-one is a ultra long acting beta$_2$-agonist. Furthermore indacaterol exhibits a longer duration of action as well as having a greater cardiovascular safety margin.

A preferred anticholinergic agent for use in the present invention is tiotropium.

Tiotropium is chemically known as (1α, 2β, 4β, 5α, 7β)-7-[(hydroxy di-2-thienyl acetyl) oxy]-9,9-di methyl-3-oxa-9-azonia tricyclo [3.3.1.0$^{2,4}$] nonane bromide monohydrate. Tiotropium has duration of action of up to 32 hours. Also tiotropium causes an improvement in dyspnea and a reduction in the need for rescue therapy.

Tiotropium in combination with pulmonary rehabilitation (PR) is associated with an increased exercise endurance time and produces clinically meaningful improvements in dyspnea and health status as compared to PR alone in COPD patients.

Further, tiotropium is more potent than ipratropium in the treatment of patients with COPD in terms of the effect of lung function, dyspnea, exacerbation rates and health status.

The terms "carmoterol", "indacaterol" and "tiotropium" are used in broad sense to include not only "carmoterol", "indacaterol" and "tiotropium" per se but also their pharmaceutically acceptable salts, pharmaceutically acceptable solvates, pharmaceutically acceptable hydrates, pharmaceutically acceptable esters, pharmaceutically acceptable enantiomers, pharmaceutically acceptable derivatives, pharmaceutically acceptable polymorphs, pharmaceutically acceptable prodrugs, etc.

The term "R (+) budesonide" is used in broad sense to include not only "R (+) budesonide" per se but also its pharmaceutically acceptable salts, pharmaceutically acceptable solvates, pharmaceutically acceptable hydrates, pharmaceutically acceptable esters, pharmaceutically acceptable derivatives, pharmaceutically acceptable polymorphs, pharmaceutically acceptable prodrugs, etc.

In accordance with the present invention, the preferred $beta_2$-agonists are: carmoterol, indacaterol, formoterol, arformoterol, salmeterol.

In accordance with the present invention, there preferred anticholinergics are: tiotropium, oxitropium, ipratropium Particularly preferred compositions according to the invention are pharmaceutical compositions in which the $beta_2$-agonist comprises or consists of carmoterol, indacaterol, formoterol, aformoterol, salmeterol, and the anticholinergic comprise or consists of tiotropium.

Particularly preferred compositions comprise:

R (+) budesonide, $beta_2$-agonist comprising carmoterol, an anticholinergic comprising tiotropium, and, optionally, one or more pharmaceutically acceptable excipients.

R (+) budesonide, $beta_2$-agonist consisting of carmoterol, an anticholinergic consisting of tiotropium, and, optionally, one or more pharmaceutically acceptable excipients.

R (+) budesonide, $beta_2$-agonist comprising indacaterol, an anticholinergic comprising tiotropium, and, optionally, one or more pharmaceutically acceptable excipients.

R (+) budesonide, $beta_2$-agonist consisting of indacaterol, an anticholinergic consisting of tiotropium, and, optionally, one or more pharmaceutically acceptable excipients.

R (+) budesonide, $beta_2$-agonist comprising formoterol, and, optionally, one or more pharmaceutically acceptable excipients.

R (+) budesonide, $beta_2$-agonist consisting of formoterol, and, optionally, one or more pharmaceutically acceptable excipients.

R (+) budesonide, $beta_2$-agonist comprising arformoterol, and, optionally, one or more pharmaceutically acceptable excipients.

R (+) budesonide, $beta_2$-agonist consisting of arformoterol, and, optionally, one or more pharmaceutically acceptable excipients.

According to the present invention, R (+) budesonide may be present in the composition in the amount of about 80 mcg to about 640 mcg.

According to the present invention, carmoterol may be present in the composition in the amount of about 1 mcg to about 4 mcg.

According to the present invention, indacaterol may be present in the composition in the amount of about 50 mcg to about 800 mcg.

According to the present invention, tiotropium may be present in the composition in the amount of about 9 mcg to about 18 mcg.

We have found that the combination therapy of R (+) budesonide, tiotropium and carmoterol and the combination therapy of R (+) budesonide, tiotropium and indacaterol provide effective methods for treating inflammatory and/or obstructive diseases of the respiratory tract, particularly COPD or asthma.

Furthermore, the combination of R (+) budesonide, tiotropium and carmoterol and the combination of R (+) budesonide, tiotropium and indacaterol provide a rapid onset of action and improved control of obstructive or inflammatory airway diseases, or reduction in the exacerbations of the diseases.

Another advantage of the combinations is that they facilitate the treatment of an obstructive and inflammatory airway disease with a single medicament.

We have further found that the combination of R (+) budesonide, tiotropium and carmoterol, and the combination of R (+) budesonide, tiotropium and indacaterol can each be administered once a day in therapeutically effective amounts.

Further this combination therapy provides for administration of the combination by use of a single inhaler for patients with severe COPD who currently have to make use of multiple inhalers. This is particularly important since COPD is a disease of the elderly who may get confused between the inhalers and who also suffer from several combined conditions such as heart disease, arthritis etc. and are receiving other medications.

The pharmaceutical compositions of the present invention may be administered by any suitable method used for delivery of drugs to the respiratory tract. The composition of the present invention may thus be administered using metered dose inhalers (MDI), dry powder inhalers (DPI), nebulisers, nasal sprays, nasal drops, insufflation powders, sprays and spray patches.

Preferred embodiments of the invention comprise pharmaceutical compositions comprising R (+) budesonide and one or more bronchodilators, which compositions are used in the form of nebulisers, dry powder inhalers (DPI), nasal sprays, nasal drops, insufflation powders, sprays and spray patches; in a particularly preferred embodiment, compositions are used in the form of metered dose inhalers (MDI).

The various dosage forms according to the present invention may comprise carriers/excipients suitable for formulating the same.

The metered dose inhalation formulations, according to the present invention may comprise one or more pharmaceutically acceptable excipients, such as HFC/HFA propellants, co-solvents, bulking agents, non volatile component, buffers/pH adjusting agents, surface active agents, preservatives, complexing agents, lubricants, antioxidants or combinations thereof.

In the context of the present invention, propellants are those substances which, when mixed with the co-solvent(s), form a homogeneous propellant system in which a therapeutically effective amount of a medicament can be dissolved. The HFC/HFA propellant must be toxicologically safe and must have a vapor pressure which is suitable to enable the medicament to be administered via a pressurized MDI.

According to the present invention the HFC/HFA propellants may comprise, one or more of 1,1,1,2-tetrafluoroethane (HFA-134(a)), 1,1,1,2,3,3,3,-heptafluoropropane (HFA-227), HFC-32 (difluoromethane), HFC-143(a) (1,1,1-trifluoroethane), HFC-134 (1,1,2,2-tetrafluoroethane), HFC-152a (1,1-difluoroethane) and such other propellants which may be known to the person having a skill in the art.

In the context of the present invention, the co-solvent is any solvent which is miscible in a formulation in the amount desired and which, when added, provides a formulation in which the medicament can be dissolved. The function of the co-solvent is to increase the solubility of the medicament and the excipients in the formulation.

According to the present invention the co-solvent may comprise one or more of $C_2$-$C_6$ aliphatic alcohols, such as but not limited to ethyl alcohol and isopropyl alcohol; glycols such as but not limited to propylene glycol, polyethylene glycols, polypropylene glycols, glycol ethers, and block copolymers of oxyethylene and oxypropylene; and other substances, such as but not limited to glycerol, polyoxyethylene alcohols, and polyoxyethylene fatty acid esters; hydrocarbons such as but not limited to n-propane, n-butane, isobutane, n-pentane, iso-pentane, neo-pentane, and n-hexane; and ethers such as but not limited to diethyl ether.

Suitable surfactants may be employed in the aerosol solution formulation of the present invention, which surfactants may serve to stabilize the solution formulation and improve the performance of valve systems within a metered dose inhaler.

According to the present invention the surfactant may comprise one or more ionic and/or non-ionic surfactant, but not limited to oleic acid, sorbitan trioleate, lecithin, isopropylmyristate, tyloxapol, polyvinylpyrrolidone polysorbates such as polysorbate 80, vitamin E-TPGS, and macrogol hydroxystearates such as macrogol-15-hydroxystearate.

In the context of the present invention, the non-volatile component is all the suspended or dissolved constituents that would be left after evaporation of the solvent.

According to the present invention, the non-volatile component may comprise one or more of monosaccharides such as but not limited to glucose, arabinose; disaccharides such as lactose, maltose; oligosaccharides and polysaccharides such as but not limited to dextrans; polyalcohol such as but not limited to glycerol, sorbitol, mannitol, xylitol; salts such as but not limited to potassium chloride, magnesium chloride, magnesium sulphate, sodium chloride, sodium citrate, sodium phosphate, sodium hydrogen phosphate, sodium hydrogen carbonate, potassium citrate, potassium phosphate, potassium hydrogen phosphate, potassium hydrogen carbonate, calcium carbonate and calcium chloride.

Suitable bulking agents may be employed in the metered dose inhalation formulations of the present invention.

According to the present invention, the bulking agent may comprise one or more saccharides, including monosaccharides, disaccharides, polysaccharides and sugar alcohols such as arabinose, glucose, fructose, ribose, mannose, sucrose, terhalose, lactose, maltose, starches, dextran or mannitol.

Suitable buffers or pH adjusting agents may be employed in the metered dose inhalation formulations of the present invention.

According to the present invention, the buffer or the pH adjusting agent may comprise one or more of organic or inorganic acids such as but not limited to citric acid, ascorbic acid, hydrochloric acid, sulfuric acid, nitric acid, or phosphoric acid.

Suitable preservatives may be employed in aerosol solution formulations of the present invention to protect such formulations from contamination with pathogenic bacteria.

According to the present invention, the preservative may comprise one or more of benzalkonium chloride, benzoic acid, benzoates such as sodium benzoate and such other preservatives which may be known to the person having a skill in the art.

Suitable complexing agents may be employed in aerosol solution formulations of the present invention, which complexing agents are capable of forming complex bonds.

According to the present invention, the complexing agent may comprise one or more of but not limited to sodium EDTA or disodium EDTA.

A further preferred embodiment of the present invention can be where the composition is in the form of insufflatable powder. R (+) budesonide in combination with one or more bronchodilator may be mixed with inert carrier substances or drawn up onto inert carrier substances to form insufflatable powders.

A dry powder insufflation composition according to the present invention can be administered by the use of an insufflator, which can produce a finely divided cloud of the dry powder. The insufflator preferably is provided with means to ensure administration of a substantially pre-determined amount of a formulation or product as provided by the present invention. The powder may be used directly with an insufflator, which is provided with a bottle or container for the powder, or the powder may be filled into a capsule or cartridge, such as a gelatin capsule, or other single dose device adapted for administration. The insufflator preferably has means to open the capsule or other dose device.

A further preferred embodiment of the present invention can be where the composition is in the form of dry powder inhaler (DPI). R (+) budesonide in combination with one or more bronchodilator may be mixed with inert carrier substances or drawn up onto inert carrier substances to form dry powder inhalation formulations.

Carrier substances suitable for forming the insufflation powders or dry powder inhalation formulations of the present invention include but are not limited to sugars/sugar alcohols such as glucose, saccharose, lactose and fructose, starches or starch derivatives, oligosaccharides such as dextrins, cyclodextrins and their derivatives, polyvinylpyrrolidone, alginic acid, tylose, silicic acid, cellulose, cellulose derivatives (for example cellulose ether), sugar alcohols such as mannitol or sorbitol, calcium carbonate, calcium phosphate, lactose, lactitol, dextrates, dextrose, maltodextrin, saccharides including monosaccharides, disaccharides, polysaccharides; sugar alcohols such as arabinose, ribose, mannose, sucrose, trehalose, maltose and dextran.

In another embodiment of the present invention the composition may be in the form of a nebuliser formulation.

Nebulisation therapy has an advantage over other inhalation therapy, since it is easy to use and does not require co-ordination or much effort. It also works much more rapidly than medicines taken by mouth.

For nebulisers, the composition according to the present invention may comprise suitable excipients such as osmotic agents, pH regulators buffering agent, wetting agent and complexing agents in a suitable vehicle.

Osmotic agents, which may be used in nebuliser formulations according to the present invention include sodium chloride, potassium chloride, zinc chloride, calcium chloride and mixtures thereof. Other suitable osmotic agents include, but are not limited to, mannitol, glycerol, dextrose and mixtures thereof.

The pH of a nebuliser formulation may be adjusted by the addition of pharmacologically acceptable acids. Pharmacologically acceptable inorganic acids or organic acids may be used for this purpose. Examples of preferred inorganic acids are selected from the group consisting of hydrochloric acid, hydrobromic acid, nitric acid, sulphuric acid and phosphoric acid and mixtures thereof. Examples of particularly suitable organic acids are selected from the group consisting of ascorbic acid, citric acid, malic acid, tartaric acid, maleic acid, succinic acid, fumaric acid, acetic acid, formic acid and propionic acid and mixtures thereof.

Complexing agents that may be used in nebuliser formulations according to the present invention include editic acid (EDTA) or one of the known salts thereof, e.g. sodium EDTA or disodium EDTA dihydrate (sodium edetate).

Wetting agents that may be used in nebuliser formulations according to the present invention include sodiumdioctylsulfosuccinate; polysorbates such as polysorbate 20, polysorbate 40, polysorbate 60, polysorbate 80, polysorbate 65, polysorbate 85; sorbitan fatty acid esters such as Span 20, Span 40, Span 60 Span 80, Span 120; sodium lauryl sulfate; polyethoxylated castor oil; polyethoxylated hydrogenated castor oil and mixtures thereof.

Anti-microbial preservative agent may also be added for multi-dose packages.

The formulation according to the present invention may be included in suitable containers provided with means enabling the application of the contained formulation to the respiratory tract. The dry powder inhalation formulations of the present invention may either be encapsulated in capsules of gelatin or HPMC, or in blisters. Alternatively, the dry powder inhalation formulations may be contained in a reservoir either in a single dose or multi-dose dry powder inhalation device. Alternatively, the dry powder inhalation formulations may be suspended in a suitable liquid vehicle and packed in an aerosol container along with suitable propellants or mixtures thereof. Further, the dry powder inhalation formulations may also be dispersed in a suitable gas stream to form an aerosol composition.

The metered dose inhalation formulations of the present invention may be packed in plain aluminium cans or in SS (stainless steel) cans. Some aerosol drugs tend to adhere to the inner surfaces, i.e. walls, of the cans and valves. This can lead to the patient getting significantly less than the prescribed amount of the active agent upon each activation of a metered dose inhaler. Coating the inner surface of the container with a suitable polymer can reduce this adhesion problem. Suitable coatings include fluorocarbon copolymers such as FEP-PES (fluorinated ethylene propylene and poly ether sulphone) and PFA-PES (perfluoro alkoxy alkane and poly ether sulphone), epoxy and ethylene. Alternatively, the inner surfaces of the cans may be anodized, plasma treated or plasma coated.

It will be understood by a person skilled in the art that the pharmaceutical composition, according to the present invention, may further comprise (i.e. in addition to the bronchodilator, i.e., the beta$_2$-agonist and/or the anticholinergic) one or more active(s) selected from antihistamines, antiallergics or leukotriene antagonist or their pharmaceutically acceptable salts, solvates, tautomers, derivatives, enantiomers, isomers, hydrates, prodrugs or polymorphs thereof.

The present invention also provides a process to manufacture the compositions according to the present invention.

Thus the present invention provides a process of preparing a metered dose inhalation formulation which process comprises admixing more or more pharmaceutically acceptable carriers and/or excipients with the actives (e.g. R (+) budesonide and one or more bronchodilators) and the propellant, and optionally providing the formulation in precrimped cans.

The present invention also provides a process of preparing a dry powder inhalation formulation which process comprises admixing of one or more pharmaceutically acceptable carriers and/or excipients with the actives (e.g. R (+) budesonide and one or more bronchodilator) and providing the formulation as a dry powder inhaler.

The present invention also provides a process of preparing an inhalation solution which process comprises dissolving the drugs, optionally chelating agents, osmotic agents and any other suitable ingredients in the vehicle and adjusting the pH using a suitable pH adjusting agent.

The present invention further provides a method for the treatment in a mammal, such as a human, for treating respiratory, inflammatory or obstructive airway disease such as COPD and asthma, which method comprises administration of a therapeutically effective amount of a pharmaceutical composition according to the present invention. The method of treatment may be characterized in that R (+) budesonide and one or more bronchodilators are administered once a day in therapeutically effective amounts, e.g. R (+) budesonide, tiotropium and carmoterol or R (+) budesonide, tiotropium and indacaterol are administered once a day in therapeutically effective amounts.

Furthermore, the present invention provides pharmaceutical compositions comprising R (+) budesonide and one or more bronchodilators for use in the prophylaxis or treatment of respiratory, inflammatory or obstructive airway disease.

The following examples are for the purpose of illustration of the invention only and are not intended in any way to limit the scope of the present invention.

Example 1

| Sr. No. | Ingredients | Qty/Can |
|---|---|---|
| 1. | R (+) Budesonide | 16 mg |
| 2. | Arformoterol tartarate | 0.48 mg |
| 3. | HFA134a | 9.6 g |

Process:

(1) R (+) Budesonide and Arformoterol tartarate were dispersed with the propellant.

(2) The suspension obtained in step (1) was filled in precrimped cans.

Example 2

| Sr. No. | Ingredients | Qty/Can |
|---|---|---|
| 1. | R (+) Budesonide | 16 mg |
| 2. | Arformoterol tartarate | 0.48 mg |
| 3. | 2% Ethanol | 0.22 g |
| 4. | 0.22% Lecithin | 0.0003 mg |
| 5. | HFA227 | 11.0 g |

Process:
(1) Lecithin was dispersed in ethanol.
(2) R (+) Budesonide and Arformoterol tartarate were dispersed in the mixture as obtained in step (1).
(3) The drug suspension was mixed with propellant HFA277.
(4) The suspension obtained in step (3) was filled in precrimped cans.

Example 3

| Sr. No. | Ingredients | Qty/Can |
|---|---|---|
| 1. | R (+) Budesonide | 16 mg |
| 2. | Arformoterol tartarate | 0.48 mg |
| 3. | HFA227 | 11.2 g |

Process:
(1) R (+) Budesonide and Arformoterol tartarate were dispersed with the propellant.
(2) The suspension obtained in step (1) was filled in precrimped cans.

Example 4

| Sr. No. | Ingredients | Qty/Can |
|---|---|---|
| 1. | R (+) Budesonide | 16 mg |
| 2. | Arformoterol tartarate | 0.48 mg |
| 3. | 0.3% PEG 1000 | 33.6 mg |
| 4. | 0.001% PVP K25 | 0.11 mg |
| 5. | HFA227 | 11.2 g |

Process:
(1) PVP was dispersed in PEG.
(2) R (+) Budesonide and Arformoterol tartarate were dispersed in the mixture as obtained in step (1).
(3) The drug suspension was mixed with propellant HFA277.
(4) The suspension obtained in step (3) was filled in precrimped cans.

Example 5

| Sr. No. | Ingredients | Qty/Can |
|---|---|---|
| 1. | R (+) Budesonide | 16 mg |
| 2. | Formoterol fumarate | 0.96 mg |
| 3. | HFA134a | 9.6 g |

Process:
(1) R (+) Budesonide and Formoterol fumarate were dispersed with the propellant.
(2) The suspension obtained in step (1) was filled in precrimped cans.

Example 6

| Sr. No. | Ingredients | Qty/Can |
|---|---|---|
| 1. | R (+) Budesonide | 16 mg |
| 2. | Formoterol fumarate | 0.96 mg |
| 3. | 2% Ethanol | 0.22 g |

-continued

| Sr. No. | Ingredients | Qty/Can |
|---|---|---|
| 4. | 0.22% Lecithin | 0.0003 mg |
| 5. | HFA227 | 11.0 g |

Process:
(1) Lecithin was dispersed in ethanol.
(2) R (+) Budesonide and Formoterol fumarate were dispersed in the mixture as obtained in step (1).
(3) The drug suspension was mixed with propellant HFA277
(4) The suspension obtained in step (3) was filled in precrimped cans.

Example 7

| Sr. No. | Ingredients | Qty/Can |
|---|---|---|
| 1. | R (+) Budesonide | 16 mg |
| 2. | Formoterol fumarate | 0.96 mg |
| 3. | HFA227 | 11.2 g |

Process:
(1) R (+) Budesonide and Formoterol fumarate were dispersed with the propellant.
(2) The suspension obtained in step (1) was filled in precrimped cans.

Example 8

| Sr. No. | Ingredients | Qty/Can |
|---|---|---|
| 1. | R (+) Budesonide | 16 mg |
| 2. | Formoterol fumarate | 0.96 mg |
| 3. | 0.3% PEG 1000 | 33.6 mg |
| 4. | 0.001% PVP K25 | 0.11 mg |
| 5. | HFA227 | 11.2 g |

Process:
(1) PVP was dispersed in PEG.
(2) R (+) Budesonide and Formoterol fumarate were dispersed in the mixture as obtained in step (1).
(3) The drug suspension was mixed with propellant HFA277.
(4) The suspension obtained in step (3) was filled in precrimped cans.

Example 9

| Sr. No. | Ingredients | Qty/Spray |
|---|---|---|
| 1. | R (+) Budesonide | 100 mcg |
| 2. | Tiotropium | 9 mcg |
| 3. | Carmoterol | 1 mcg |
| 4. | HFA134A or HFA227 | q.s |

Process:
(1) R (+) Budesonide, Tiotropium and Carmoterol were homogenized with a part quantity of HFA.
(2) The suspension obtained in step (1) was transferred to the mixing vessel where the remaining quantity of HFA was added.

(3) The resulting suspension was mixed, recirculated and filled into pre-crimped aluminum cans.

Example 10

| Sr. No. | Ingredients | Qty/Spray |
| --- | --- | --- |
| 1. | R (+) Budesonide | 100 mcg |
| 2. | Tiotropium | 9 mcg |
| 3. | Carmoterol | 1 mcg |
| 4. | Lactose | 100% of the drug |
| 5. | HFA134A or HFA227 | q.s. |

Process:

(1) R (+) Budesonide, Tiotropium and Carmoterol were homogenized with lactose and a part quantity of HFA.

(2) The suspension obtained in step (1) was transferred to the mixing vessel where the remaining quantity of HFA was added.

(3) The resulting suspension was mixed, recirculated and filled in into pre-crimped aluminum cans.

Example 11

| Sr. No. | Ingredients | Qty/Spray |
| --- | --- | --- |
| 1. | R (+) Budesonide | 100 mcg |
| 2. | Tiotropium | 9 mcg |
| 3. | Carmoterol | 1 mcg |
| 4. | PEG400/1000 | 0.3% of total formulation |
| 5. | PVP K 25 | 0.001% of total formulation |
| 6. | HFA134A or HFA227 | q.s. |

Process:

(1) PVP was dissolved in PEG and part quantity of HFA.

(2) The solution obtained in step (1) was transferred to a mixing vessel.

(3) R (+) Budesonide, Tiotropium and Carmoterol were homogenized with a part quantity of HFA.

(4) The suspension obtained in step (3) was transferred to the mixing vessel where remaining quantity of HFA was added.

(5) The resulting total suspension was mixed, recirculated and filled in into pre-crimped aluminum cans.

Example 12

| Sr. No. | Ingredients | Qty/Spray |
| --- | --- | --- |
| 1. | R (+) Budesonide | 100 mcg |
| 2. | Tiotropium | 9 mcg |
| 3. | Carmoterol | 1 mcg |
| 4. | Ethanol | 15-20% of total formulation |
| 5. | Glycerol | 1% of total formulation |
| 6. | HCL (0.08N) | pH 2.5-3.5 |
| 7. | HFA134a | q.s. |

Process:

(1) Glycerol was dissolved in ethanol and required quantity of HCl was added.

(2) R (+) Budesonide, Tiotropium and Carmoterol were dissolved in the solution obtained in step (1).

(3) The resulting solution was transferred to the mixing vessel where HFA was added.

(4) The resulting solution was mixed, recirculated and filled in into pre-crimped aluminum cans.

Example 13

| Sr. No. | Ingredients | Qty/Spray |
| --- | --- | --- |
| 1. | R (+) Budesonide | 100 mcg |
| 2. | Tiotropium | 9 mcg |
| 3. | Carmoterol | 1 mcg |
| 4. | Ethanol | 15-20% of total formulation |
| 5. | HCL (0.08N) | pH 2.5-3.5 |
| 6. | HFA134a | q.s. |

Process:

(1) Required quantity of HCl was added to ethanol.

(2) R (+) Budesonide, Tiotropium and Carmoterol were dissolved in the solution obtained in step (1).

(3) The resulting solution was transferred to the mixing vessel where HFA was added.

(4) The resulting solution was mixed, recirculated and filled in into pre-crimped aluminum cans.

Example 14

| Sr. No. | Ingredients | Qty/Spray |
| --- | --- | --- |
| 1. | R (+) Budesonide | 100 mcg |
| 2. | Tiotropium | 9 mcg |
| 3. | Carmoterol | 1 mcg |
| 4. | Ethanol | 15-20% of total formulation |
| 5. | Glycerol | 1% of total formulation |
| 6. | Citric acid anhydrous | pH 2.5-3.5 |
| 7. | HFA134a | q.s. |

Process:

(1) Required quantity of citric acid and glycerol was added to ethanol.

(2) R (+) Budesonide, Tiotropium and Carmoterol were dissolved in the solution obtained in step (1).

(3) The resulting solution was transferred to the mixing vessel where HFA was added.

(4) The resulting solution was mixed, recirculated and filled in into pre-crimped aluminum cans.

Example 15

| Sr. No. | Ingredients | Qty/Spray |
| --- | --- | --- |
| 1. | R (+) Budesonide | 100 mcg |
| 2. | Tiotropium | 9 mcg |
| 3. | Carmoterol | 1 mcg |
| 4. | Ethanol | 15-20% of total formulation |
| 5. | Citric acid anhydrous | pH 2.5-3.5 |
| 6. | HFA134a | q.s. |

Process:

(1) Required quantity of citric acid was added to ethanol.

(2) R (+) Budesonide, Tiotropium and Carmoterol were dissolved in the solution obtained in step (1).

(3) The resulting solution was transferred to the mixing vessel where HFA was added.

(4) The resulting solution was mixed, recirculated and filled in into pre-crimped aluminum cans.

Example 16

| Sr. No. | Ingredients | Qty/Spray |
|---|---|---|
| 1. | R (+) Budesonide | 100 mcg |
| 2. | Tiotropium | 9 mcg |
| 3. | Carmoterol | 1 mcg |
| 4. | Ethanol | 1-2% of total formulation |
| 5. | Lecithin | 0.02% of the drug |
| 6. | HFA134a or HFA227 | q.s. |

Process:

(1) Required quantity of lecithin was added to ethanol.

(2) Tiotropium and Carmoterol were homogenized with part quantity of HFA and transferred to the mixing vessel.

(3) R (+) Budesonide was homogenized with the solution obtained from step (1) and part quantity of HFA.

(4) The suspension obtained in step (4) was transferred to the mixing vessel where the remaining quantity of HFA was added.

(5) The resulting suspension is then mixed, recirculated and filled in into pre-crimped aluminum cans.

Example 17

| Sr. No. | Ingredients | Qty/Spray |
|---|---|---|
| 1. | R (+) Budesonide | 100 mcg |
| 2. | Tiotropium | 9 mcg |
| 3. | Carmoterol | 1 mcg |
| 4. | Ethanol | 1-2% of total formulation |
| 5. | Oleic acid | 0.02-5% of the drug |
| 6. | HFA134a or HFA227 | q.s. |

Process:

(1) Required quantity of oleic acid was added to ethanol.

(2) Tiotropium and Carmoterol were homogenized with part quantity of HFA and transferred to the mixing vessel.

(3) R (+) Budesonide was homogenized with the solution obtained from step (1) and part quantity of HFA.

(4) The suspension obtained in step (4) was transferred to the mixing vessel where remaining quantity of HFA was added.

(5) The resulting suspension is then mixed, recirculated and filled in into pre-crimped aluminum cans.

Example 18

| No. | Ingredients | Qty/Unit |
|---|---|---|
| 1 | R (+) Budesonide | 0.160 mg |
| 2 | Carmoterol | 0.002 mg |
| 3 | Tiotropium Bromide Monohydrate | 0.0225 mg |
| 4 | Lactose monohydrate | 24.8155 mg |
|   | Total | 25.000 mg |

Process:

(1) R (+) Budesonide, Caromoterol, Tiotropium Bromide Monohydrate were sifted with a part quantity of lactose.

(2) The cosift of step (1) was then sifted with the remaining quantity of lactose and blended.

(3) The blend of step (2) was then filled in capsules.

Example 19

| No. | Ingredients | Qty/Unit |
|---|---|---|
| 1 | R (+) Budesonide | 0.640 mg |
| 2 | Carmoterol | 0.004 mg |
| 3 | Tiotropium Bromide Monohydrate | 0.0225 mg |
| 4 | Lactose monohydrate | 24.3335 mg |
|   | Total | 25.0000 mg |

Process:

(1) R (+) Budesonide, Caromoterol, Tiotropium Bromide Monohydrate were sifted with a part quantity of lactose.

(2) The cosift of step (1) was then sifted with the remaining quantity of lactose and blended.

(3) The blend of step (2) was then filled in capsules.

Example 20

| Sr. No. | Ingredients | Qty/Spray |
|---|---|---|
| 1. | R (+) Budesonide | 100 mcg |
| 2. | Tiotropium | 9 mcg |
| 3. | Indacaterol | 50 mcg |
| 4. | HFA134A or HFA227 | q.s |

Process:

(1) R (+) Budesonide, Tiotropium and Indacaterol were homogenized with a part quantity of HFA.

(2) The suspension obtained in step 1 was transferred to the mixing vessel where the remaining quantity of HFA was added.

(3) The resulting suspension was mixed, recirculated and filled in into pre-crimped aluminum cans.

Example 21

| Sr. No. | Ingredients | Qty/Spray |
|---|---|---|
| 1. | R (+) Budesonide | 100 mcg |
| 2. | Tiotropium | 9 mcg |
| 3. | Indacaterol | 50 mcg |
| 4. | Lactose | 100% of the drug |
| 5. | HFA134A or HFA227 | q.s. |

Process:

(1) R (+) Budesonide, Tiotropium and Indacaterol were homogenized with lactose and a part quantity of HFA.

(2) The suspension obtained in step 1 was transferred to the mixing vessel where the remaining quantity of HFA was added.

(3) The resulting suspension was mixed, recirculated and filled in into pre-crimped aluminum cans.

Example 22

| Sr. No. | Ingredients | Qty/Spray |
|---|---|---|
| 1. | R (+) Budesonide | 100 mcg |
| 2. | Tiotropium | 9 mcg |
| 3. | Indacaterol | 50 mcg |
| 4. | PEG400/1000 | 0.3% of total formulation |
| 5. | PVP K 25 | 0.001% of total formulation |
| 6. | HFA134A or HFA227 | q.s. |

Process:
(1) PVP was dissolved in PEG and part quantity of HFA.
(2) The solution obtained in Step 1 was transferred to a mixing vessel.
(3) R (+) Budesonide, Tiotropium and Indacaterol were homogenized with a part quantity of HFA.
(4) The suspension obtained in step 3 was transferred to the mixing vessel where remaining quantity of HFA was added.
(5) The resulting total suspension was mixed, recirculated and filled in into pre-crimped aluminum cans.

Example 23

| Sr. No. | Ingredients | Qty/Spray |
|---|---|---|
| 1. | R (+) Budesonide | 100 mcg |
| 2. | Tiotropium | 9 mcg |
| 3. | Indacaterol | 50 mcg |
| 4. | Ethanol | 15-20% of total formulation |
| 5. | Glycerol | 1% of total formulation |
| 6. | HCL (0.08N) | pH 2.5-3.5 |
| 7. | HFA134a | q.s. |

Process:
(1) Glycerol was dissolved in ethanol and required quantity of HCl was added.
(2) R (+) Budesonide, Tiotropium and Indacaterol were dissolved in the solution obtained in step (1).
(3) The resulting solution was transferred to the mixing vessel where HFA was added.
(4) The resulting solution was mixed, recirculated and filled in into pre-crimped aluminum cans.

Example 24

| Sr. No. | Ingredients | Qty/Spray |
|---|---|---|
| 1. | R (+) Budesonide | 100 mcg |
| 2. | Tiotropium | 9 mcg |
| 3. | Indacaterol | 50 mcg |
| 4. | Ethanol | 15-20% of total formulation |
| 5. | HCL (0.08N) | pH 2.5-3.5 |
| 6. | HFA134a | q.s. |

Process:
(1) Required quantity of HCl was added to ethanol.
(2) R (+) Budesonide, Tiotropium and Indacaterol were dissolved in the solution obtained in step (1).
(3) The resulting solution was transferred to the mixing vessel where HFA was added.
(4) The resulting solution was mixed, recirculated and filled in into pre-crimped aluminum cans.

Example 25

| Sr. No. | Ingredients | Qty/Spray |
|---|---|---|
| 1. | R (+) Budesonide | 100 mcg |
| 2. | Tiotropium | 9 mcg |
| 3. | Indacaterol | 50 mcg |
| 4. | Ethanol | 15-20% of total formulation |
| 5. | Glycerol | 1% of total formulation |
| 6. | Citric acid anhydrous | pH 2.5-3.5 |
| 7. | HFA134a | q.s. |

Process:
(1) Required quantity of citric acid and glycerol was added to ethanol.
(2) R (+) Budesonide, Tiotropium and Indacaterol were dissolved in the solution obtained in step (1).
(3) The resulting solution was transferred to the mixing vessel where HFA was added.
(4) The resulting solution was mixed, recirculated and filled in into pre-crimped aluminum cans.

Example 26

| Sr. No. | Ingredients | Qty/Spray |
|---|---|---|
| 1. | R (+) Budesonide | 100 mcg |
| 2. | Tiotropium | 9 mcg |
| 3. | Indacaterol | 50 mcg |
| 4. | Ethanol | 15-20% of total formulation |
| 5. | Citric acid anhydrous | pH 2.5-3.5 |
| 6. | HFA134a | q.s. |

Process:
1) Required quantity of citric acid was added to ethanol.
2) R (+) Budesonide, Tiotropium and Indacaterol were dissolved in the solution obtained in step (1).
3) The resulting solution was transferred to the mixing vessel where HFA was added.
4) The resulting solution was mixed, recirculated and filled in into pre-crimped aluminum cans.

Example 27

| Sr. No. | Ingredients | Qty/Spray |
|---|---|---|
| 1. | R (+) Budesonide | 100 mcg |
| 2. | Tiotropium | 9 mcg |
| 3. | Indacaterol | 50 mcg |
| 4. | Ethanol | 1-2% of total formulation |
| 5. | Lecithin | 0.02 of the API |
| 6. | HFA134a or HFA227 | q.s. |

Process:
1) Required quantity of lecithin was added to ethanol.
2) Tiotropium and Indacaterol were homogenized with part quantity of HFA and transferred to the mixing vessel.

3) R (+) Budesonide was homogenized with the solution obtained from step (1) and part quantity of HFA.
4) The suspension obtained in step (4) was transferred to the mixing vessel where remaining quantity of HFA was added.
5) The resulting suspension is then mixed, recirculated and filled in into pre-crimped aluminum cans.

Example 28

| Sr. No. | Ingredients | Qty/Spray |
|---|---|---|
| 1. | R (+) Budesonide | 100 mcg |
| 2. | Tiotropium | 9 mcg |
| 3. | Indacaterol | 50 mcg |
| 4. | Ethanol | 1-2% of total formulation |
| 5. | Oleic acid | 0.02-5% of the drug |
| 6. | HFA134a or HFA227 | q.s. |

Process:
1) Required quantity of oleic acid was added to ethanol.
2) Tiotropium and Indacaterol were homogenized with part quantity of HFA and transferred to the mixing vessel.
3) R (+) Budesonide was homogenized with the solution obtained from step (1) and part quantity of HFA.
4) The suspension obtained in step (4) was transferred to the mixing vessel where the remaining quantity of HFA was added.
5) The resulting suspension is then mixed, recirculated and filled in into pre-crimped aluminum cans.

Example 29

| No. | Ingredients | Qty/Unit |
|---|---|---|
| 1 | R (+) Budesonide | 0.160 mg |
| 2 | Indacaterol maleate | 0.1944 mg |
| 3 | Tiotropium Bromide Monohydrate | 0.0225 mg |
| 4 | Lactose monohydrate IP/Ph.Eur/NF | 24.6231 mg |
| | Total | 25.000 mg |

Process:
(1) R (+) Budesonide, Indacaterol maleate, Tiotropium Bromide Monohydrate were sifted with a part quantity of lactose.
(2) The cosift of step (1) was then sifted with the remaining quantity of lactose and blended.
(3) The blend of step (2) was then filled in capsules.

Example 30

| No. | Ingredients | Qty/Unit |
|---|---|---|
| 1 | R (+) Budesonide | 0.640 mg |
| 2 | Indacaterol maleate | 0.3888 mg |
| 3 | Tiotropium Bromide Monohydrate | 0.0225 mg |
| 4 | Lactose monohydrate IP/Ph.Eur/NF | 23.9487 mg |
| | Total | 25.0000 mg |

Process:
(1) R (+) Budesonide, Indacaterol maleate, Tiotropium Bromide Monohydrate were sifted with a part quantity of lactose.
(2) The cosift of step 1 was then sifted with the remaining quantity of lactose and blended.
(3) The blend of step 2 was then filled in capsules.

It will be readily apparent to one skilled in the art that varying substitutions and modifications may be made to the invention disclosed herein without departing from the spirit of the invention. Thus, it should be understood that although the present invention has been specifically disclosed by the preferred embodiments and optional features, modification and variation of the concepts herein disclosed may be resorted to by those skilled in the art, and such modifications and variations are considered to fall within the scope of the invention.

It is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It must be noted that, as used in this specification and the appended claims, the singular forms "a," "an" and "the" include plural references unless the context clearly dictates otherwise. Thus, for example, reference to "an excipient" includes a single excipient as well as two or more different excipients, and the like.

What is claimed is:

1. A pharmaceutical composition for use in treatment of at least one of asthma and COPD comprising a fixed dose combination consisting of R-(+)-budesonide and arformoterol, and, optionally, one or more pharmaceutically acceptable excipients,
   wherein R (+) budesonide is present in an amount ranging from 80-640 mcg and arformoterol is present in an amount ranging from 2.4-20.4 mcg; and,
   wherein said fixed dose combination of the R-(+)-budesonide and arformoterol is formulated for administration once per day.

2. A pharmaceutical composition according to claim 1, formulated as an inhalation composition.

3. A pharmaceutical composition according to claim 1, formulated for use in a metered dose inhaler.

4. A pharmaceutical composition according to claim 3, comprising a propellant.

5. A pharmaceutical composition according claim 1, comprising an excipient selected from a co-solvent, an antioxidant, a surfactant, a bulking agent and a lubricant.

6. A pharmaceutical composition according to claim 1, formulated for use as a dry powder inhalation formulation.

7. A pharmaceutical composition according to claim 1, comprising at least one finely divided pharmaceutically acceptable carrier suitable for use in dry powder inhalation formulations.

8. A combination composition according to claim 7, wherein said carrier includes a saccharide and/or a sugar alcohol.

9. A combination composition according to claim 1, formulated for use as an inhalation solution.

10. A combination composition according to claim 9, comprising an excipient selected from a wetting agent, osmotic agent, a pH regulator, a buffering agent and a complexing agent, provided in a pharmaceutically acceptable vehicle.

11. A pharmaceutical composition according to claim 1, formulated for inhalation, for use as a nasal spray, for use as nasal drops, for use as an insufflation powder, or for use as a spray patch.

12. A pharmaceutical composition for use in treatment of at least one of asthma and COPD comprising a fixed dose combination consisting of R-(+)-budesonide and arformoterol, and, optionally, one or more pharmaceutically acceptable excipients,
formulated in a metered multi-dose container, wherein the metered multi-dose container contains (quantity/container):
R (+) Budesonide 16 mg, and
Arformoterol tartarate 0.48 mg;
wherein said fixed dose combination of the R-(+)-budesonide and arformoterol is formulated for administration once per day.

13. A pharmaceutical composition according to claim 12, wherein the metered multi-dose container further contains one or more propellants selected from:
1,1,1,2-tetrafluoroethane,
1,1,1,2,3,3,3,-heptafluoropropane,
difluoromethane,
1,1,1-trifluoroethane,
1,1,2,2-tetrafluoroethane, and
1,1-difluoroethane.

14. A pharmaceutical composition according to claim 12, wherein the metered multi-dose container contains (quantity/container):
R (+) Budesonide 16 mg,
Arformoterol tartarate 0.48 mg, and
1,1,1,2-tetrafluoroethane (HFA-134(a)) propellant 9.6 g.

15. A pharmaceutical composition according to claim 12, wherein the metered multi-dose container contains (quantity/container):
R (+) Budesonide 16 mg,
Arformoterol tartarate 0.48 mg,
2% Ethanol 0.22 g,
0.22% Lecithin 0.0003 mg, and
1,1,1,2,3,3,3,-heptafluoropropane (HFA-227) propellant 11.0 g.

16. A pharmaceutical composition according to claim 12, wherein the metered multi-dose container contains (quantity/container):
R (+) Budesonide 16 mg,
Arformoterol tartarate 0.48 mg, and
1,1,1,2,3,3,3,-heptafluoropropane (HFA-227) propellant 11.2 g.

17. A pharmaceutical composition according to claim 12, wherein the metered multi-dose container contains (quantity/container):
R (+) Budesonide 16 mg,
Arformoterol tartarate 0.48 mg,
0.3% PEG 1000 33.6 mg,
0.001% polyvinylpyrrolidone (PVP K25) 0.11 mg, and
1,1,1,2,3,3,3,-heptafluoropropane (HFA-227) propellant 11.2 g.

18. A pharmaceutical composition according to claim 12, comprising at least one finely divided pharmaceutically acceptable carrier suitable for use in dry powder inhalation formulations.

19. A combination composition according to claim 18, wherein said carrier includes a saccharide and/or a sugar alcohol.

20. A combination composition according to claim 12, formulated for use as an inhalation solution.

21. A combination composition according to claim 20, comprising an excipient selected from a wetting agent, osmotic agent, a pH regulator, a buffering agent and a complexing agent, provided in a pharmaceutically acceptable vehicle.

22. A pharmaceutical composition according to claim 12, formulated for inhalation, for use as a nasal spray, for use as nasal drops, for use as an insufflation powder, or for use as a spray patch.

* * * * *